United States Patent
Lindh et al.

[11] Patent Number: 5,316,546
[45] Date of Patent: May 31, 1994

[54] JOINT

[76] Inventors: Leif Lindh, Klockar Malms Vag 13, S-182 34 Danderyd; Peter Kohler, Apelvagen 27, S-182 75 Stocksund, both of Sweden

[21] Appl. No.: 854,985
[22] PCT Filed: Oct. 26, 1990
[86] PCT No.: PCT/SE90/00696
 § 371 Date: Apr. 30, 1992
 § 102(e) Date: Apr. 30, 1992
[87] PCT Pub. No.: WO91/06267
 PCT Pub. Date: May 16, 1991

[30] Foreign Application Priority Data
Oct. 31, 1989 [SE] Sweden .................. 8903645

[51] Int. Cl.$^5$ ........................... A61F 5/01
[52] U.S. Cl. ........................... 602/16; 602/26
[58] Field of Search ........... 602/16, 26, 27, 62, 602/21; 128/80 C, 80 F, 80 H; 623/18, 39

[56] References Cited

U.S. PATENT DOCUMENTS

| | | |
|---|---|---|
| 3,990,116 | 11/1976 | Fixel et al. . |
| 4,130,115 | 12/1978 | Taylor .................. 602/16 |
| 4,366,813 | 1/1983 | Nelson .................. 602/26 |
| 4,727,862 | 3/1988 | Waddell et al. .......... 602/16 |

FOREIGN PATENT DOCUMENTS

| | | |
|---|---|---|
| 101132 | 3/1965 | Denmark .......... 128/80 C |
| 838479 | 5/1952 | Fed. Rep. of Germany .... 128/80 F |
| 451110 | 9/1987 | Sweden . |

Primary Examiner—Richard J. Apley
Assistant Examiner—Beverly A. Meindl
Attorney, Agent, or Firm—Nixon & Vanderhye

[57] ABSTRACT

A hinge for use in an orthosis having the function of supporting, protecting and/or controlling a body joint. The hinge includes first and second sets of flexible, substantially planar, elongated strip-shaped elements mutually slidable in a plane-to-plane contacting relationship. The strip-shaped elements are carried by supporting members having a controlling and guiding function and at least one of the sets of strip-shaped elements is comprised of resilient strip elements having a degree of springiness and stiffness and being resiliently flexible in the longitudinal direction of the strip yet essentially rigid against bending about an axis essentially perpendicular to the hinge axis of the joint. The second set of strip-shaped elements is of a lower degree of springiness and stiffness than the first set and serves as spacer elements having the function of guiding and supporting the resilient elements such that the spacing between the elements is maintained constant along substantially the entire length of the elements. At least one of the strip shaped elements of both the first and second sets is fixed at its opposite ends with a means being provided for the supporting members to move when the hinge is flexed or extended.

6 Claims, 12 Drawing Sheets

FIG. 9(a)  FIG. 9(c)  FIG. 9(e) 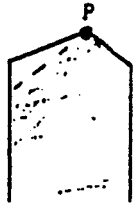
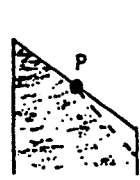 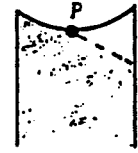 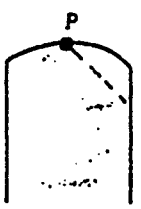
FIG. 9(b) FIG. 9(d) FIG. 9(f)

FIG. 11
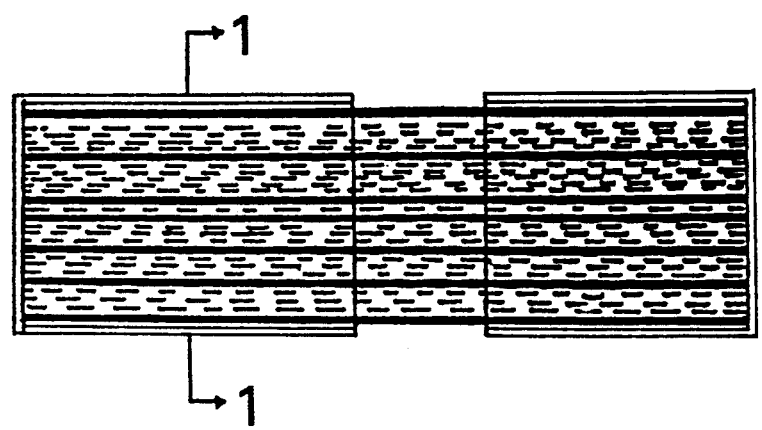
FIG. 11(a)   FIG. 11(c)   FIG. 11(e)
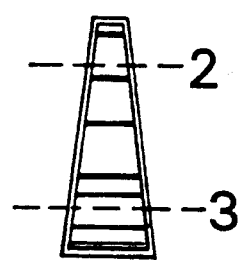  
 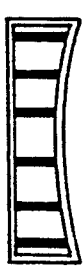
FIG. 11(b)   FIG. 11(d)

JOINT

The invention relates to a hinge intended to be used preferably in an orthosis and has the function of supporting, protecting and/or guiding a body joint, said hinge including at least two flexible, essentially strip shaped elements arranged mutually slidable in a plane-to-plane relationship, which elements are carried by supporting members having a controlling and guiding function.

The present invention provides a hinge which is to form part of some kind of joint supporting or protecting bandage, orthosis, or to form part of a device intended to support or stiffen one or more bodily joints. The hinge can also be applied for prophylactic purposes in order to prevent injury in sports practice or in other physical activity, or to consolidate a joint which has been injured or operated upon, or to limit the range of movement of the joint, or to facilitate control or guidance of one or more joints of the body.

Usually orthoses, i.e. joint supporting bandages, include pivot means of the hinge type provided on either side of the joint of the body, e.g. the knee joint. These orthosis hinges have essential disadvantages. Firstly, they are usually provided with hinge pivots which impart to the articulation of the orthosis a stationary pivot axis, as distinguished from an anatomic joint whose axis of articulation is displaced, for example, in movement of the joint. This displacement between the orthosis and the part of the body must be assumed by the adjacent soft tissues. Furthermore, such a hinge based articulation in the orthosis does not offer any possibility of performing the rotation which takes place in e.g. the final phase of knee extension, and also this movability in relation to the orthosis must be assumed by the soft tissues. Prophylactic use of hinge pivots is hardly possible as, in order to offer adquate strength, they must be made so large that there will be a risk of injury not only to the wearer but also to other persons participating in the activity.

A knee orthosis, for example, must allow extension and flexion, should protect against violence sideways and frontways, and possibly also prevent hyperextension.

The problem of the locked and immovable pivot axis has been solved, at least in part, by means of another type of hinge disclosed in the German Patent Specification No. 838 479, where the hinge includes a plurality of thin steel leaf springs placed one upon the other in a similar way as in a laminated type spring. However, in order to afford sufficient lateral and rotational stability, particularly if only one spring assembly is to be used on the outside of the knee, the hinge will become too stiff in flexing to be usable in practice.

Another type of hinge, which also offers at least some adaption to the anatomic joint, is disclosed in the U.S. Pat. No. 4,130,115. The hinge disclosed therein comprises two opposite holders or housings, each provided with a plurality of elongated flexible rib elements spaced to form interspaces, so that the ribs of one housing are slideably received between the ribs of the other housing.

These ribs are secured in the housing elements in such a way that they will define grooves wherein the ribs of the opposite housing element are slideably received. This requires that the two housing elements have different widths. The hinge is made of plastics so that it can be washed and cleaned together with the orthosis or bandage. In order to be able to alter the strength of this hinge the distance between the two housing elements is adjusted. It is thus quite clear that this is a type of ready-made hinge which cannot readily be adjusted to a particular application. In the type of design presented in this U.S. patent application the two housing elements must definitely have the same longitudinal extension (cf. FIG. 1 of the U.S. patent specification), which clearly illustrates the inconvenience involved by this inflexibility. Obviously the hinge cannot in a smooth and simple way be adapted to the configuration of the leg. As to the strength of the hinge there is no great variability, as one is limited to alter this strength merely by means of the distance between the housing elements. In addition, due to its structure this hinge develops a friction which is double that developed by the hinge according to the invention.

A hinge of this type could hardly be provided with the desired flexibility and at the same time offer sufficient lateral strength to permit it to be used only on the outside of the knee. Consequently the hinge would hardly allow rotation and thus not make room for the above mentioned rotation in the final phase of the knee movement. Instead, adaption is carried out by the rotational movement being compensated by the soft tissues of the leg assuming the same. Also, in all probability this hinge cannot assume vertical loads. This type of hinge can scarcely be limited as to its range of motion, a capacity which is an important property of the hinge according to our invention. The hinge according to our invention, with its present design, can also be limited as to its range of motion in order to prevent violation caused by superextension.

A further type of hinge is disclosed in the Swedish Patent No. 8503612-7, which hinge is in the form of a single hinge, that is, it is intended to be placed on one side of a joint of the body. Of course it can also be used in combination with a further hinge placed on the opposite side of the bodily joint to be supported.

The hinge described in the above Swedish patent comprises two opposite holders or housings each receiving the opposite ends of a number of strip shaped elements. These elements are maintained at a mutual predetermined and constant distance from each other, and partly by using said housing elements, partly by using rigid spacer members provided in the central portion of the strip elements. These spacer members have a limited extension lengthwise of the strip elements, which causes the distance between the strip elements to vary in accordance with the degree of flexion of the hinge.

It has now turned out that this hinge has certain deficiencies Due to its structure it is clumsy to use. The central portion accommodates a large space which means that besides the end pieces the hinge includes a further part which represents a risk of injury. Owing to its design the hinge will show certain specific properties which are predetermined at manufacture.

The present invention has for its object to eliminate most deficiencies of the hinges previously known. The hinges already known are cut and dried products. That means that although the assortment is large, in all probalitiy, problems will still arise when the orthosis hinge is adapted to the anatomic joint. Neither must problems of a cosmetic nature be neglected. The known hinges are difficult to apply to various joints of the body in a manner which is satisfactory from an esthetic view-point. A further drawback of the known hinges is the fact that the distribution of forces within the hinge is established at manufacture and cannot be efficiently changed. Although the hinge of Swedish Patent No. 8503612-7 is a definite improvement in comparison with prior art hinges, it exhibits a certain instability in certain applications. In order to solve these problems the present invention provides a new hinge.

The present hinge is characterized by the feature that at least one of these strip shaped elements comprises a resilient strip element having a high degree springiness and of a high stiffness, which element is resiliently flexible in the longitudinal direction of the strip, about an axis located in the main plane of the strip, essentially perpendicular to the longitudinal direction of the strip, but which is essentially rigid against bending about an axis essentially perpendicular to the main plane and longitudinal direction of the strip, the remaining strip elements having lower degree of springiness and a less stiffness than the resilient strip elements, to serve as spacer elements having a function of guiding and supporting the resilient strip elements and having essentially the same longitudinal extension as the resilient elements so that in flexing the hinge the spacing of the strip shaped elements is maintained constant along substantially the whole extension of the strip shaped elements, and in that at least one of the strip shape elements, preferably at least one of the resilient strip elements, is directly or indirectly fixed at both ends. Means are also provided to allow the supporting members to move, when the hinge is flexed or extended, along curves which are defined mutually and relatively in dependence of the flexion and extension, which curves are determined by the hinge movement.

The invention will now be described with reference to the accompanying figures which show diagrammatically examples of embodiments:

FIG. 9, illustrates a diagrammatical view of a number of possible embodiments of the abutment, that is, the bottoms of the support elements, and empty spaces arranged in the support elements in order to make room for the strip elements and the resilient elements in joint articulation, and also locking means.

FIG. 11, illustrates embodiments of the hinge according to FIG. 1, and in FIGS. 11a–e examples of cross-sections through the hinge along line A—A in FIG. 11 (11e corresponds to a parted support element).

Figure 1:
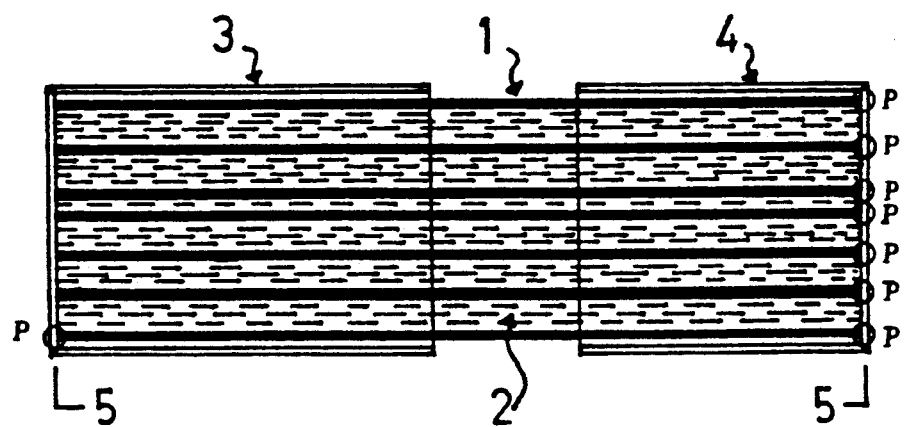
FIG. 1, illustrates the hinge in its basic design.

The hinge shown in FIG. 1 includes strip or rib elements 1 made of spring steel or a material of corresponding qualities. Spacer elements 2 are interleaved between the strip shaped elements 1, which spacer elements, for example, are made of teflon or a similar material, have a coefficient of friction adapted to the specific use and which have essentially the same area as the strip elements 1. The ends of the strip and spacer elements are inserted into pocket like support elements 3, 4 (carrying members having a guiding function). A locking device (5) is indicated at one end of the two support elements. Locking members to maintain the elements spaced at a predetermined distance from each other provided in both support elements, which members lock one or more of the strip elements, whereof at least one is locked at both ends. The design of this locking member is not critical as long as it fulfils its intended function to prevent the hinge from falling apart and also to define the range of motion and the strength of the hinge. When it comes to locking one or more elements to the support element said locking member is preferably arranged in the form of a pin or the like passing completely or partly through the support elements. If all strip shaped elements in a support element is to be locked this can of course be carried out in some other suitable way, for example, by glueing or the like. The strip element or elements used for locking longer than the remaining strips in order to make room for locking this very strip element or elements.

In all figures locations contemplated for locking are marked P.

Figure 2:
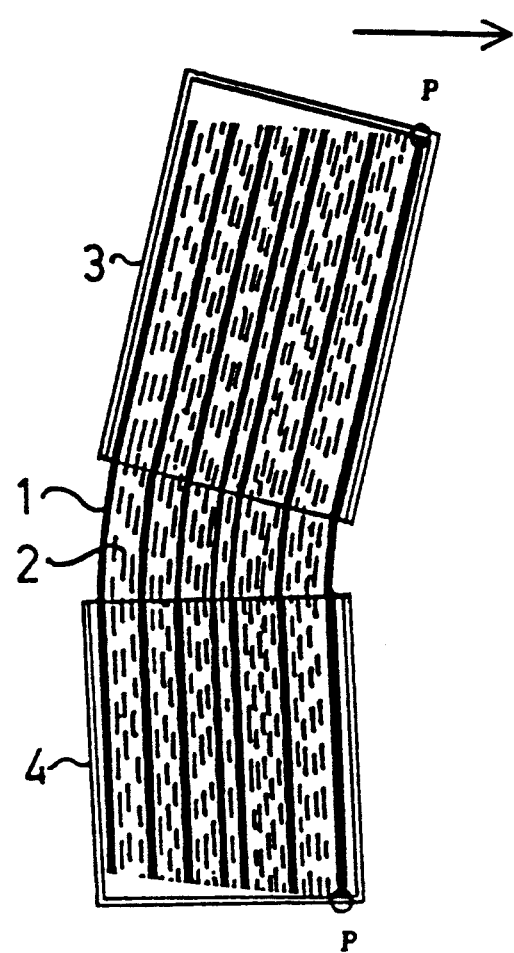
FIG. 2, illustrates the hinge according to FIG. 1 in a flexed position.

In FIG. 2 the same hinge as in FIG. 1 is shown but in a bent or flexed condition. It can be seen that the hinge is locked on its right side and that a free space will arise on the left side of the support elements where strip and spacer elements no longer reach down to the bottom of the respective support element at the bending. In the figure arrows illustrate conceivable directions of movement of the hinge.

Figure 3:
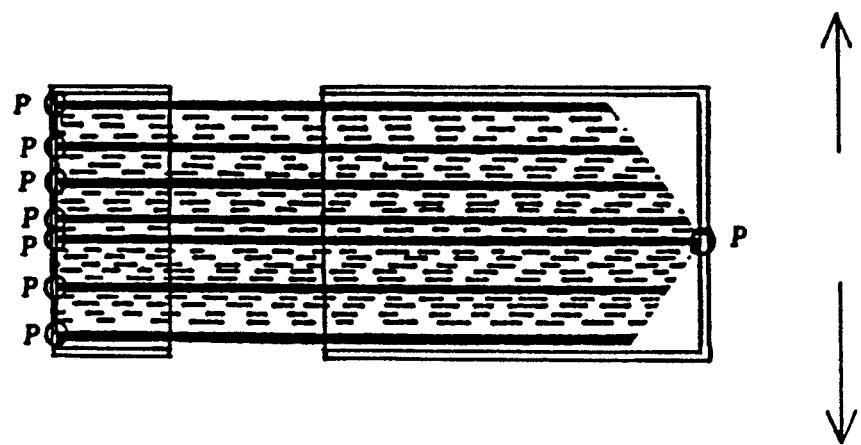
FIG. 3, illustrates embodiment of the hinge according to FIG. 1.

In FIG. 3 there is shown an embodiment of the hinge according to FIG. 1 where one of the support elements has been shortened for e.g. space reasons or cosmetic reasons.

In comparison with FIG. 1 of the above U.S. patent specification it is easy to see why a support element has been shortened. In addition, this is an essential difference between the hinge according to our invention and the hinge of the U.S. patent, where it is not possible, because of its structure, to shorten onesidedly one of the support elements.

In FIGS. 1–5 the support elements 3, 4 have been drawn as square, hollow pockets wherein the strip elements 1 and spacer elements 2 are introduced, but within the scope of the invention the support element design can be widened to include in general an abutment (a bottom) in the pocket whose curve line describes the same curve line as the motion of the hinge. The bottom can also be formed as an inverted V-like curve or assume other forms conditioned by the specific application and the specific body joint for which the hinge is intended. In addition, the support elements can be bestowed a curved form corresponding longitudinally to the body joint concerned in order that the hinge be adjusted to the body joint.

Figure 4:
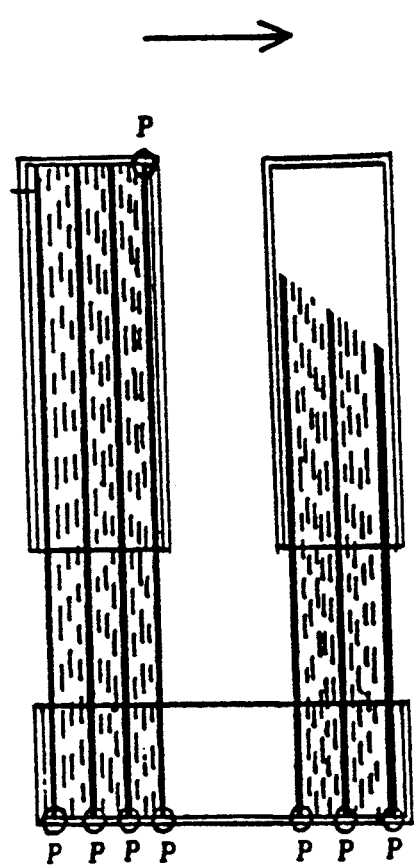
FIG. 4, illustrates the hinge according to FIG. 3 where the longer housing has been parted.
Figure 5:
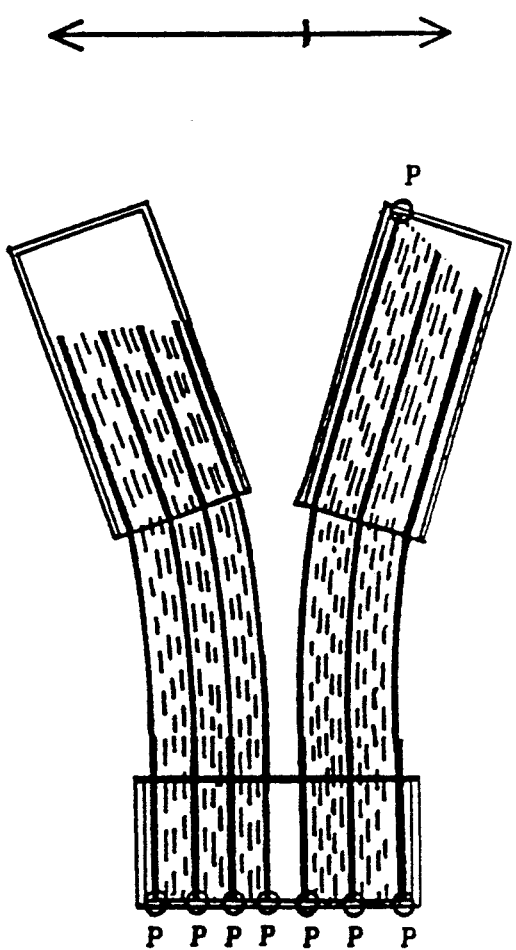
FIG. 5, illustrates embodiment of the hinge according to FIG. 4.

FIGS. 4 and 5 illustrate how the longer support element has been divided lenghtwise in two parts. This structure can be useful for application on certain body joints in order to provide a smooth and flexible orthosis. The hinge shown in FIG. 5 is provided with preformed bent strip elements which can render a further gain of space possible.

It should also be pointed out that in certain specific cases of loss of function, when the extending muscles work but the flexing muscles do not, there is a possibility to provide a hinge which is preflexed, that is, the strip elements are preformed so that a bent orthosis is obtained. Here the wearer can use his tensioning muscles to straighten the body joint after which, when the tensioning muscles are relaxed, a return movement of the body joint to a flexed position is brought about.

Figure 6:
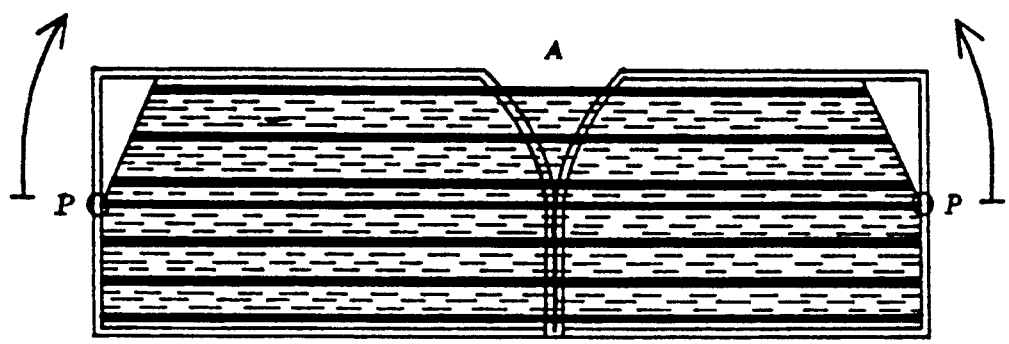
FIG. 6, illustrates embodiment of the hinge according to FIG. 1.

In FIG. 6 it is shown how it is possible e.g. to arrange a stable locking of the hinge in one direction of movement thereof. In the opposite direction the range of movement is controlled, on the one hand, by the shape of the support element exterior at A and, on the other hand, by the free space existing at top right and top left in the support elements and which is created by adjusting, in accord with the application, the length of the strip and spacer elements. Preferably one of the central strip elements is locked, see the figure.

Figure 7:
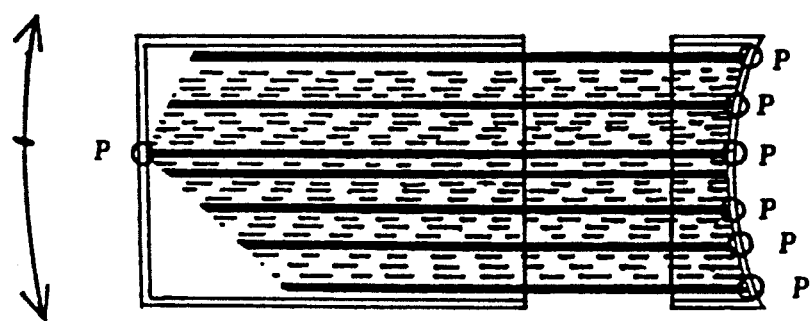
FIG. 7, illustrates embodiment of the hinge according to FIG. 1.

The embodiment shown in FIG. 7 is particularly intended to make room for anatomical prominences. The shape of the short support element can of course be modified as desired, but the figure illustrates the basic principle.

Figure 8:
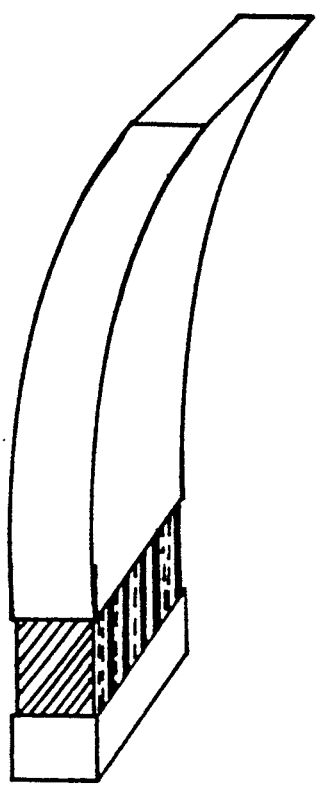
FIG. 8, illustrates embodiment of the hinge according to FIG. 1, viewed in elevation and wherein one support element (the one having a controlling function) exhibits in plane a curved surface.
Figure 10A:
FIG. 10, illustrates examples of the design of strip element and spacer element.
Figure 10B:
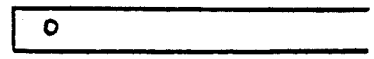
Figure 10C:
Figure 10D:
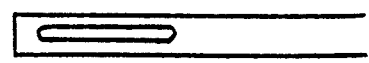
Figure 10E:
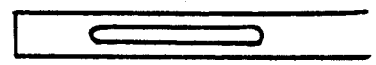
Figure 10F:
Figure 10G:

In FIG. 8 a support element of a specific design is examplified. This support element is associated with a particular form of the strip and spacer elements (see FIG. 10g). The surface of the support element, curved longitudinally, creates a rotation when flexing the hinge. This rotation is determined by the radius of curvature.

In FIG. 9 it is exemplified how the bottom (abutment) of the support element can be formed, locking of an element at the point designated P being proposed. The non-hatched part of the respective support element shows that part which can be left more or less empty, by those strip and/or spacer elements located on the corresponding place being adapted to make room for the movement of the elements when the hinge is flexed.

In FIG. 10 some examples are shown of various embodiments of strip and spacer elements, respectively. The apertures marked in FIGS. 10b and 10c are intended for locking the hinge, and the slits marked in 10d and 10e are provided in order to make it possible to lock one or two strips only, in which case the remaining strips will not hamper, thanks to the slits, the movability of the hinge. As a matter of course slits of this type can also be used for limiting the range of movement, possibly in combination with the design of the strip and spacer elements. In FIG. 10f there is shown, instead of slits, an alternative design. At the bottom of FIG. 10 an element is shows which is designed for use in a hinge according to FIG. 8.

As can be seen the present invention is based on the feature that the hinge hereof has been considerably simplified, thereby gaining greater flexibility, which previously has not been possible to attain with prior hinges. The new hinge is based on the feature, as we have seen, that one or more stiff but resilient strip elements are provided between two end pieces. Between these strip elements an optional number of spacer elements are interleaved as desired, for example, when adjusting the hinge to the individual concerned or the purpose concerned, which spacer elements exhibit essentially the same surface area as the stiff but resilient strip elements. Within the scope of the invention and in accordance with the function desired the spacer elements can be flat, tape formed, circular, oval, or trapezoidal. Strips of the type here shown are of course also useable for limiting the range of movement. Also, the spacer elements can be provided as desired with a wedge-shaped cross section (e.g. for use in a support element of a design similar to that of FIG. 11b), and, moreover, they can vary as to their width, one edge of the elements then possibly being even and the other uneven.

The apertures and the slits can be provided when manufacturing the strip, or they can be suitably placed when the hinge is assembled.

FIG. 11 illustrates how the shape of the support elements can appear in cross section. FIGS. 11a-d all show a section through the support element along line A—A in FIG. 11. The support element shown in FIG. 11a has a configuration narrower at the dashed line A and wider at the dashed line B. The line A and B, respectively, show the limit positions of the hinge axis in relation to an imagined joint, in particular the knee joint. That is to say that one line corresponds to the position of the axis when the leg is straight and the other line to the axis position when the leg is bent. This arrangement enables the present hinge to be stronger in one position than in another, to make it possible to adjust protection so that it will fit the need of strength in various situations. FIG. 11b shows a cosmetic hinge design having the capacity to follow the shape of the leg. FIG. 11c shows a further embodiment. FIG. 11d represents a further design for adjusting purpose, possibly also for offering a possibility to change the strength of the hinge. Finally, as shown in FIG. 11e, these embodiments can be parted (cf. FIG. 4, 5, for example).

Figure 12:
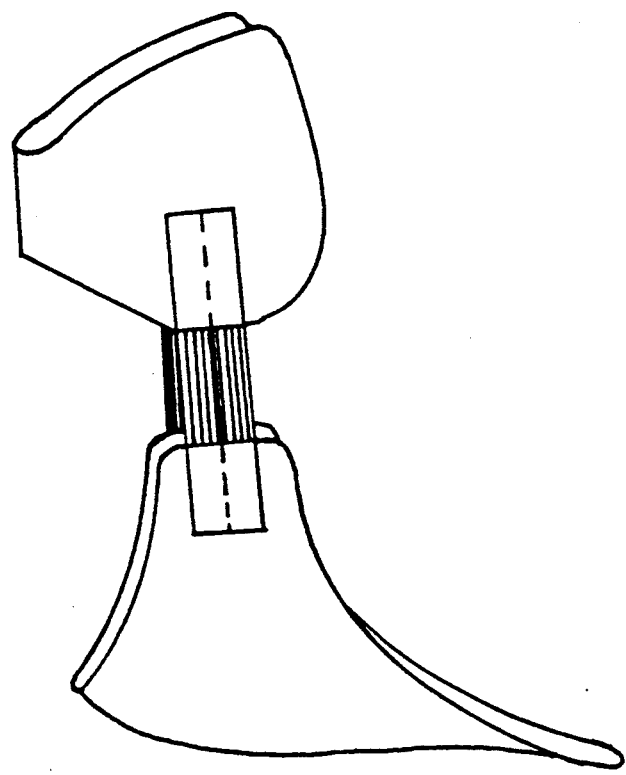
FIG. 12, illustrates the hinge provided in an ankle-joint support.

FIG. 12 shows the hinge mounted in an ankle support. This ankle support, or this joint orthosis, comprises two parts. One U-shaped part grasps around the ankle from behind and one bottom part comprises an "insertion" placed under the heel and possibly the instep and having end pieces placed on either side of the heel, this bottom part being made in one piece. The bottom part and the U-shaped part are united, by way of the end pieces, on either side of the foot joint by means of a hinge according to the invention. This foot support (joint orthosis) can of course be designed in a plurality of ways whereof the present one only represents an embodiment. This joint orthosis can either be placed loosely in a shoe, possibly lined and cushioned where appropriate, or it can be mounted in a shoe already when this is manufactured.

Figure 13:
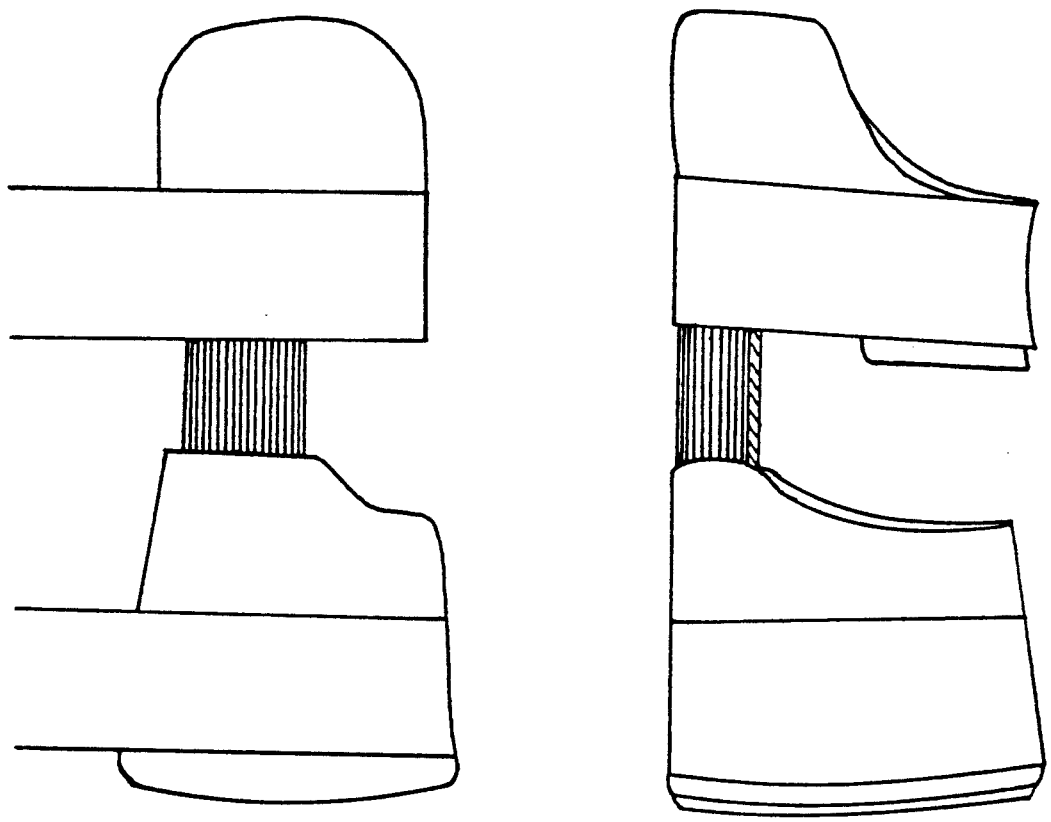
FIG. 13, illustrates the hinge provided in a wrist orthosis.

FIG. 13 shows a wrist support, which is primarily intended to support the wrist when exercising movements which can stress the joint and bring with it a risk of injury thereto. It can of course also be used for controlling or limiting the range of movement of the wrist, or for other purposes such as, for example, to train a particular movement of joint. The wrist orthosis sown in FIG. 13 comprises substantially three parts is. One part is intended to rest against the topside of the hand, one part intended to grasp the arm at the wrist, and one part connects to the hinge according to the invention. This wrist orthosis can suitbly be provided with a hook and loop type fastening means on the two parts which secure the orthosis about the wrist. It can also be provided with a glove of the type used within various branches of sports, the glove being secured in a suitable manner.

As a matter of course, the embodiments shown in the figures and described in the aforegoing only represent examples of design within the scope of the invention. To summarize the possibilities offered when it comes to vary the properties of the joint when assembling and mounting the same it could be said that 1) the number of strip elements in relation to spacer elements can be varied as desired in order to attain desired effects,
2) the distribution of the strip elements in relation to the spacer elements affects the strength of the hinge,
3) by designing the support elements differently in relation to the strip and spacer elements ranges of motion of varying size can be allowed in the hinge,
4) by designing the cross sectional shape of the support elements the strength of the hinge at different positions of the anatomical joint axis can be varied,
5) by locking an optional element or elements specific properties can be imparted to the hinge and, of course, the properties of the hinge with respect to strength and flexibility can be affected by the material of the strip elements as also by the material of the spacer elements, where the spacer elements need not necessarily be flat but can have a slightly oval shape in order to change e.g. the lateral stability of the hinge, or said elements can show some other of the designs mentioned in the description.

This hinge can thus be assembled and prepared for that very situation and for that very individual concerned, and we have obtained a smooth and readily adaptable joint which, beyond the technical improvement it represents, also means that it will provide, thanks to its smoothness, an attractive alternative in the prophylactic use of joint supporting and joint stabilizing orthoses.

We claim:

1. A hinge for supporting, protecting and/or controlling an anatomical joint, comprising first and second sets of flexible, substantially planar, elongated strip-shaped elements mutually slidable in a plane-to-plane contacting relationship, supporting members for carrying said elements, at least one of said sets of strip-shaped elements being comprised of resilient strip elements having a degree of springiness and stiffness, and resiliently flexible in their longitudinal directions about hinge axes located in the plane of the respective strips substantially perpendicular to the longitudinal direction of the strips, said one set of elements being substantially rigid against bending about an axis perpendicular to their planes and longitudinal directions of said first set of strip-shaped elements, said second set of strip-shaped elements having a lesser degree of springiness and stiffness that said first set of resilient strip-shaped elements with the elements of said first set interleaved with the elements of said second set and the elements of said second set contacting, guiding and supporting the resilient strip-shaped elements of said first set thereof on opposite sides of and coincident with said hinge axes, said elements of said second set thereof having substantially the same longitudinal extension as the resilient elements of said first set thereof so that upon flexing the hinge the spacing of the strip-shaped element is maintained constant along substantially the whole extension of the strip-shaped elements and in that at least one of the strip-shaped elements of said first and second sets thereof is fixed at its opposite ends and means enabling said supporting members to move, when the body joint is flexed or extended, along curves dependent on the magnitude of flexion and extension, and which curves are determined by the hinge movement.

2. A hinge according to claim 1 wherein said enabling means comprises a locking member disposed in one of said supporting member for locking said one strip element in a respective supporting member, said locking member engaging in an aperture in said one strip element.

3. A hinge according to claim 2, wherein said locking member is arranged in the supporting member to pass through apertures provided in a predetermined number of said strip elements, and slits or recesses provided in the remaining elements not being locked.

4. A hinge according to claim 1 wherein one or more of said strip-shaped elements are longer than remaining elements thereof, a locking member connected to a portion of the one or more longer strips in excess of the length of the remaining strip elements.

5. A hinge according to claim 1 wherein, to limit the range of motion of the hinge, each of said members has abutments configured and spaced one from the other, to provide a stop at one extreme of the range of motion of the hinge.

6. A hinge according to claim 1 wherein at least one of said supporting members is curved.

* * * * *